US00PP23856P2

(12) United States Plant Patent
Bräunig

(10) Patent No.: US PP23,856 P2
(45) Date of Patent: Aug. 27, 2013

(54) ***VERBENA* PLANT NAMED 'FLORBENACHER'**

(50) Latin Name: *Verbena×hybrida*
Varietal Denomination: Florbenacher

(75) Inventor: Tobias Michael Bräunig, Quedlinburg (DE)

(73) Assignee: Florensis Quedlinburg GmbH, Quedlinburg (DE)

( * ) Notice: Subject to any disclaimer, the term of this patent is extended or adjusted under 35 U.S.C. 154(b) by 0 days.

(21) Appl. No.: 13/507,942

(22) Filed: Aug. 8, 2012

(51) Int. Cl.
*A01H 5/00* (2006.01)

(52) U.S. Cl.
USPC ..... Plt./308

(58) Field of Classification Search
USPC ..... Plt./308
See application file for complete search history.

*Primary Examiner* — June Hwu
*Assistant Examiner* — Louanne Krawczewicz Myers
(74) *Attorney, Agent, or Firm* — Audrey Charles

(57) ABSTRACT

A new and distinct cultivar of *Verbena* plant named 'Florbenacher', characterized by its dark rose-colored flowers with a white "eye", medium green-colored foliage, and moderately vigorous, spreading growth habit, is disclosed.

1 Drawing Sheet

Latin name of genus and species of plant claimed: *Verbena×hybrida.*

Variety denomination: 'Florbenacher'.

BACKGROUND OF THE INVENTION

The present invention relates to a new and distinct cultivar of *Verbena* plant botanically known as *Verbena×hybrida* and hereinafter referred to by the cultivar name 'Florbenacher'.

The new cultivar originated in a controlled breeding program in Quedlinburg, Germany during August 2008. The objective of the breeding program was the development of *Verbena* cultivars with unique flower coloration and a trailing, spreading growth habit.

The new *Verbena* cultivar is the result of open-pollination. The female (seed) parent of the new cultivar is the proprietary *Verbena×hybrida* breeding selection coded 2101-1, not patented, characterized by its medium rose-colored flowers with a white "eye", medium green-colored foliage, and vigorous, trailing growth habit. The male (pollen) parent of the new cultivar is unknown. The new cultivar was discovered and selected as a single flowering plant within the progeny of the above stated open-pollination during August 2009 in a controlled environment in Quedlinburg, Germany.

Asexual reproduction of the new cultivar by terminal stem cuttings since August 2009 in Quedlinburg, Germany and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Florbenacher' as a new and distinct cultivar of *Verbena* plant:

1. Dark rose-colored flowers with a white "eye";
2. Medium green-colored foliage; and
3. Moderately vigorous, spreading growth habit.

Plants of the new cultivar differ from plants of the female parent primarily in having a darker rose-colored flower and reduced growth vigor.

Of the many commercially available *Verbena* cultivars, the most similar in comparison to the new cultivar is Empress Burgundy Charme 'Duempburcha', U.S. Plant Pat. No. 21,641. However, in side by side comparisons, plants of the new cultivar differ from plants of 'Duempburcha' in at least the following characteristics:

1. Plants of the new cultivar are shorter than plants of 'Duempburcha'; and
2. Plants of the new cultivar have a flower color different from plants of 'Duempburcha'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Florbenacher'. The plants were grown in 4-inch pots for 6 weeks in a greenhouse in West Chicago, Ill. Plants were given one pinch at transplant.

DETAILED BOTANICAL DESCRIPTION

Figure 1:
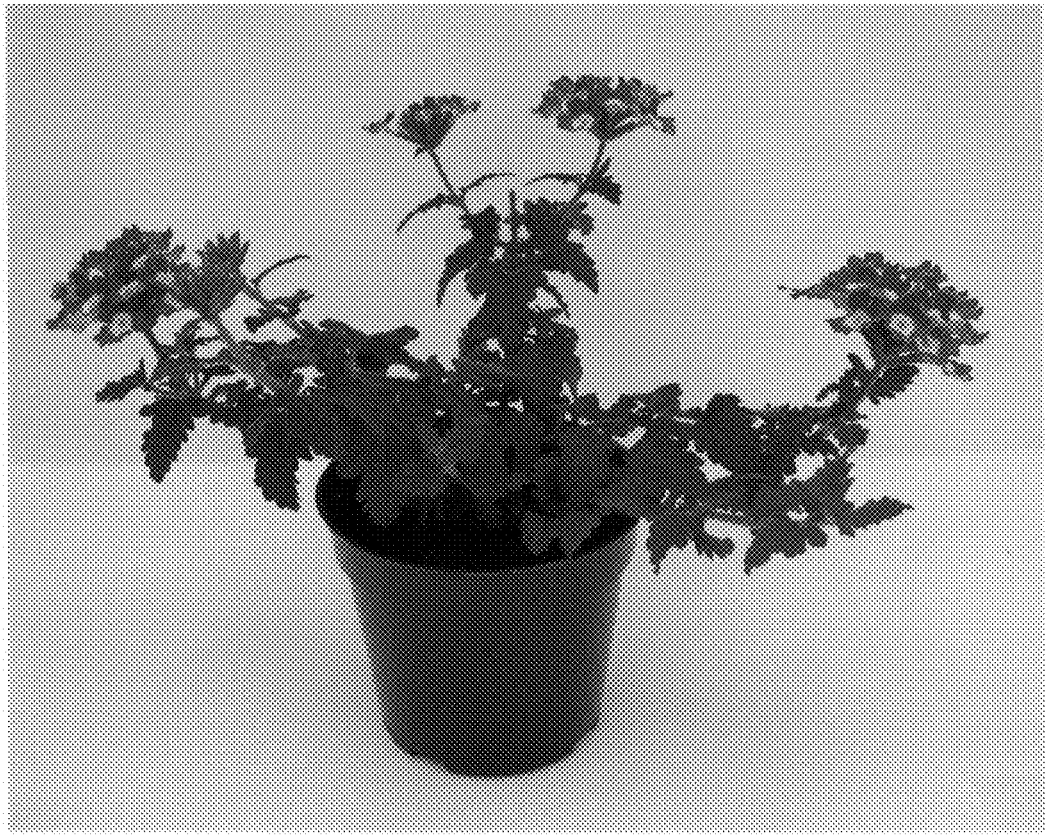
FIG. 1 illustrates a side view of the overall growth and flowering habit of 'Florbenacher'.
Figure 2:
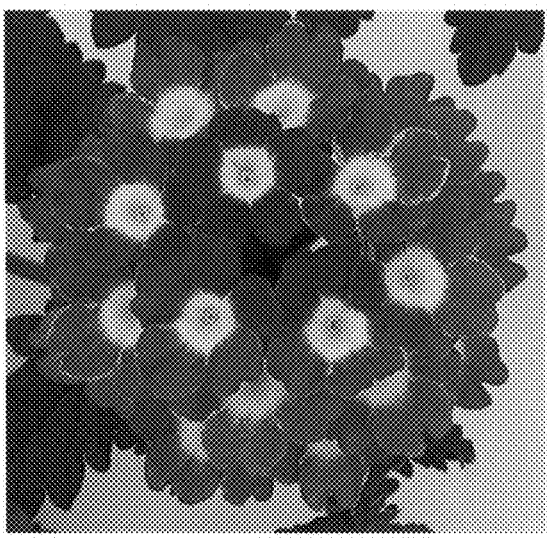
FIG. 2 illustrates a close-up view of an individual inflorescence of 'Florbenacher'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in April 2012 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4-inch pots for 6 weeks utilizing a soilless growth medium. Plants were given one pinch at transplant. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Verbena×hybrida* cultivar Florbenacher.

Parentage:

*Female parent.*—Proprietary *Verbena×hybrida* breeding selection coded 2101-1, not patented.

*Male parent.*—Unknown.

Propagation:

*Type cutting.*—Terminal stem.

*Time to initiate roots.*—Approximately 6 to 9 days.

*Time to produce a rooted cutting.*—Approximately 24 to 28 days.

*Root description.*—Fibrous.

*Rooting habit.*—Freely branching.

Plant description:

*Commercial crop time.*—Approximately 5 to 7 weeks from a rooted cutting to finish in a 10 cm pot.

*Growth habit and general appearance.*—Moderately vigorous, spreading.

*Size.*—Height from soil level to top of plant plane: Approximately 7.5 cm. Width: Approximately 40.3 cm.

*Branching habit.*—Freely branching, pinching enhances basal branching. Quantity of main branches per plant: Approximately 5.

*Branch.*—Shape: Square in cross section. Strength: Strong. Length: Approximately 21.8 cm. Diameter: Approximately 3.0 mm. Length of central internode: Approximately 2.2 cm. Texture: Densely pubescent with a mixture of glandular and nonglandular hairs. Gland color: Colorless, transparent. Color of young and mature stems: 144A.

Foliage description:

*General description.*—Quantity of leaves per main branch: Approximately 20. Fragrance: None. Form: Simple. Arrangement: Opposite.

*Leaves.*—Aspect: Perpendicular to stem. Shape: Ovate. Margin: Serrate. Apex: Acute. Base: Truncate. Venation pattern: Pinnate. Length of mature leaf: Approximately 3.6 cm. Width of mature leaf: Approximately 2.6 cm. Texture of upper surface: Moderately pubescent. Texture of lower surface: Densely pubescent with a mixture of glandular and nonglandular hairs. Gland color: Colorless, transparent. Color of upper surface of young and mature foliage: Closest to N137A with venation of 144D. Color of lower surface of young and mature foliage: 138B with venation of 145C.

*Petiole.*—Length: Approximately 7.0 mm. Diameter: Approximately 2.0 mm. Texture: Densely pubescent with a mixture of glandular and nonglandular hairs. Gland color: Colorless, transparent. Color: 144D.

Flowering description:

*Flowering habit.*—'Florbenacher' is freely flowering under outdoor growing conditions with substantially continuous blooming from spring through autumn and year-round in greenhouse environment.

*Lastingness of individual flower on the plant.*—Approximately 5 to 7 days.

Inflorescence description:

*General description.*—Type: Corymb. Shape: Hemispherical. Quantity per plant: Approximately 3. Fragrance: None. Length or height: Approximately 3.5 cm. Width: Approximately 5.7 cm. Quantity of fully open flowers per inflorescence: Approximately 18.

*Peduncle.*—Strength: Strong. Aspect: Erect. Length: Approximately 2.5 cm. Diameter: Approximately 2.0 mm. Texture: Densely pubescent with a mixture of glandular and nonglandular hairs. Gland color: Colorless, transparent. Color: 144A.

Flower description:

*General description.*—Type: Sessile, salverform.

*Bud.*—Rate of opening: Generally takes 2 to 3 days for bud to progress from first color to fully open flower. Quantity of unopened inflorescences per plant: Approximately 1.

*Bud just before opening.*—Shape: Elongated. globular at apex. Length: Approximately 1.3 cm. Diameter: Approximately 3.0 mm. Color: N81A.

*Corolla.*—Shape: Round. Diameter: Approximately 2.0 cm. Depth: Approximately 2.8 cm.

*Petals.*—Quantity: 5, fused at base forming a tube. Shape: Obovate. Appearance: Velvety. Margin: Entire. Apex: Emarginate. Length of upper petals from tube: Approximately 9.0 mm. Width of upper petals: Approximately 6.0 mm. Length of lateral petals from tube: Approximately 9.0 mm. Width of lateral petals: Approximately 7.0 mm. Length of lower petal from tube: Approximately 1.0 cm. Width of lower petal: Approximately 9.0 mm. Texture of upper surface: Glabrous. Texture of lower surface: Sparsely pubescent with a mixture of glandular and nonglandular hairs. Gland color: Colorless, transparent. Color of upper surface when fully open: Closest to 71A fades to 72B with age, base of NN155D forming an "eye", and 145B at corolla tube opening. Color of lower surface when fully open: 71D with base of NN155D. Whisker color surrounding the upper surface opening of the corolla tube: 155D.

*Corolla tube.*—Length: Approximately 1.9 cm. Diameter at proximal end: Approximately 1.0 mm. Diameter at distal end: Approximately 2.0 mm. Texture of inner and outer surfaces: Densely pubescent. Color of inner and outer surfaces: 145D at proximal end transitioning to 145B at distal end.

*Calyx.*—Shape: Tubular with 5 acute tips. Length: Approximately 1.2 cm. Width:

Approximately 2.0 mm.

*Sepals.*—Quantity per flower: 5, fused at base. Shape: Linear. Margin: Entire. Apex: Acute Length: Approximately 1.2 cm. Width: Approximately 1.0 mm. Texture of inner surface: Moderately pubescent. Texture of outer surface: Densely pubescent with a mixture of glandular and nonglandular hairs. Gland color: Colorless, transparent. Color of upper and lower surfaces: 137A, transparent where margins fuse.

*Stipules.*—Shape: Lanceolate. Apex: Acute. Length: Approximately 6.0 mm. Width at base: Approximately 2.0 mm. Texture of inner surface: Glabrous. Texture of outer surface: Densely pubescent with a mixture of glandular and nonglandular hairs. Gland color: Colorless, transparent. Color of inner and outer surfaces: 144A at base transitioning to 137A at apex.

*Reproductive organs.*—Androecium: Stamen quantity: 4, didynamous. Stamen length of longer pair: Approximately 3.0 mm. Stamen length of shorter pair: Approximately 2.0 mm. Anther shape: Bilobed, ovoid. Anther length: Approximately 1.0 mm. Anther color: 144C. Pollen amount: Moderate. Pollen color: 11D. Gynoecium: Pistil quantity: 1 per flower. Pistil length: Approximately 1.8 cm. Stigma shape: Biparted. Stigma length: Less than 1.0 mm. Stigma color: 143A. Style length: Approximately 1.7 cm. Style color: 144C transitioning to 144D at base. Ovary diameter: Approximately 1.0 mm. Ovary texture: Glabrous. Ovary color: 143A.

Seed and fruit production: Neither seed nor fruit production has been observed.

Disease and pest resistance: Resistance to pathogens and pests common to *Verbena* has not been observed.

What is claimed is:

1. A new and distinct cultivar of *Verbena* plant named 'Florbenacher', substantially as herein shown and described.

* * * * *